United States Patent [19]

Olson

[11] Patent Number: 6,124,130
[45] Date of Patent: Sep. 26, 2000

[54] MICROBIAL CATALYST FOR DESULFURIZATION OF FOSSIL FUELS

[75] Inventor: Gregory J. Olson, Arvada, Colo.

[73] Assignee: Clean Diesel Technologies, Inc., Stamford, Conn.

[21] Appl. No.: 09/131,685

[22] Filed: Aug. 10, 1998

[51] Int. Cl.$^7$ ..................................... C12S 1/02
[52] U.S. Cl. ..................... 435/282; 435/29; 435/252.4; 435/253.2; 435/253.3
[58] Field of Search ........................... 435/29, 34, 252.34, 435/252.4, 253.2, 253.3, 262, 262.5, 282, 872, 874

[56] References Cited

U.S. PATENT DOCUMENTS

| | | | |
|---|---|---|---|
| 2,641,564 | 6/1953 | Zobell | 195/3 |
| 4,562,156 | 12/1985 | Isbister et al. | 435/253 |
| 4,805,535 | 2/1989 | Isbister | 435/252 |
| 5,002,888 | 3/1991 | Kilbane, II | 435/252.31 |
| 5,104,801 | 4/1992 | Kilbane | 435/282 |
| 5,132,219 | 7/1992 | Kilbane | 435/195 |
| 5,232,854 | 8/1993 | Monticello | 435/282 |
| 5,344,778 | 9/1994 | Kilbane | 435/262 |
| 5,356,813 | 10/1994 | Monticello | 435/282 |
| 5,358,869 | 10/1994 | Kilbane | 435/282 |
| 5,387,523 | 2/1995 | Monticello | 435/282 |
| 5,468,826 | 11/1995 | Johnson et al. | 435/130 |
| 5,472,875 | 12/1995 | Monticello | 435/282 |
| 5,593,889 | 1/1997 | Valentine | 435/282 |

OTHER PUBLICATIONS

Foght et al., "Microbial Desulfurization of Petroleum," pp. 379–399. No Date Provided.

Kim et al., "Petroleum Desulfurization by *Desulfovibrio desulfuricans* M6 Using Electrochemically Supplied Reducing Equivalent," pp. 757–760. No Date Provided.

van Afferden et al., "Degradation of dibenzothiophene by Brevibacterium sp.DO," *Arch Microbiol.*, 1990, pp. 324–328.

Gallagher et al., "Microbial desulfurization of dibenzothiophene: A sulfur–specific pathway," *FEMS Microbiology Letters* 107 (1993), pp. 31–36.

Izumi et al., "Selective Desulfurization of Dibenzothiophene by *Rhodococus erythropolis* D–1," *Applied and Environmental Microbiology*, Jan. 1994, pp. 223–226.

Wang et al., "Kinetic Analyses of Desulfurization of Dibenzothiophene by *Rhodocuccus erythropolis* in Batch and Fed–Batch Cultures," *Applied and Environmental Microbiology*, May 1996, pp. 1670–1675.

Olson, "Prospects for biodesulfurization of coal: mechanisms and related process deisgns," *Fuel Processing Technology* 40 (1994), pp. 103–114.

Kargi et al., Biological Removal of Pyritic Sulfur from Coal by the Thermophilic Organism *Sulfolobus acidocaldarius, Biotechnology and Bioengineering*, vol. XXVII, pp. 41–49 (1985).

Bailey, J.E. & Ollis, D.V., Biochemical Engineering Fundamentals, McGraw–Hill, New York: 1977.

Dahlberg, M.D., et al., Fuel 71 (1993), pp. 1645–1650. (copy on order).

Rhee, S.K., et al. Applied Environmental Microbiology 64 (1998), pp. 2327–2331.

Kilbane et al., "Biodesulfurization of Water–Soluble Coal–Derived Material by *Rhodoccus rhodochrous* IGTS8," Biotechnology & Bioengineering, vol. 40, pp. 1107–1114 (1992).

Omori et al., "Desulfurization of Dibenzothiophen by *Corynbacterium* sp. Strain SY1, "Applied and Environment Microbiology, Mar. 1992, pp. 911–915.

Kilbane et al., "Biodesulfurization of Water–Soluble Coal–Derived Material by *Rhodoccus rhodochrous* IGTS8, "Biotechnology & Bioengineering, vol. 40, pp. 1107–1114 (1992).

*Primary Examiner*—William H. Beisner
*Attorney, Agent, or Firm*—Ware, Fressola, van der Sluys & Adolphson LLP

[57] ABSTRACT

Sulfur is removed from fossil fuels containing sulfur by incubation of the fuel with microbes isolated and purified from soil or water that selectively extract the sulfur without apparently utilizing the fuel as a carbon or energy source. Preferred biodesulfurization microbes remove at least about 20% of the sulfur. The microbes are obtained in a multi-step screen that first selects microorganisms that utilize dibenzothiophene (DBT) as a sole source of sulfur, and then tests these in incubations with fossil fuels; organisms that desulfurize DBT without metabolizing the DBT phenyl ring structures and desulfurize fuels only when a second carbon source devoid of sulfur is present are identified and employed in desulfurization processes. Two cultures, CDT-4 and CDT-4b, were particularly efficacious in the desulfurization of liquid fossil fuels.

14 Claims, No Drawings

MICROBIAL CATALYST FOR DESULFURIZATION OF FOSSIL FUELS

TECHNICAL FIELD

This invention relates to isolated and purified microorganisms that desulfurize fossil fuels without concomitant metabolism of the hydrocarbon value of the fuels, and to methods of using these microorganisms.

Sulfur occurs ubiquitously in fossil fuels. In petroleum, it is the third most abundant element after carbon and hydrogen, and yet it is an undesirable component of both raw and refined fuels. Sulfur in petroleum contributes to problems of corrosion of materials, particularly metals, during the refining process. In addition, combustion of sulfur-containing fuels results in sulfur dioxide pollution of the atmosphere, contributing to acid rain. Consequently, strict regulations on sulfur emissions and the sulfur content of refined fuels have been adopted in the U.S. and elsewhere.

Most fuel desulfurization methods currently used are chemical and/or physical processes. Many of these processes, such as hydrodesulfurization, typically require hydrogen and high temperatures and pressures, and hydrogenation catalysts are often poisoned by the hydrogen sulfide formed in the reaction. The methods can therefore become costly. Moreover, a certain fraction of sulfur in fossil fuels, especially aromatic sulfur such as benzothiophenes and dibenzothiophenes, is refractory to hydrodesulfurization. Thus, additional treatments to reduce the sulfur content of refined fuels are often required.

Furthermore, the world supply of low-sulfur petroleum is decreasing, resulting in increased interest in heavy crudes and oil shales having higher sulfur contents. These mature oils have higher concentrations of refractory sulfur in the form of stable dibenzothiophenes. In fact, dibenzothiophene is frequently the major thiophenic compound in mature and altered high-sulfur crude oil, comprising, for example, up to 70% of the organic sulfur in some Texas oils (Foght, J. M, et al., in Ehrlich, H. L., and Brierley, C. L., eds., *Microbial Mineral Recovery*, McGraw-Hill, New York, 1990, p. 382).

Biodesulfurization, particularly of high-sulfur content petroleums, theoretically is an attractive alternative to hydrodesulfurization because of costs benefit from reduced temperature and pressure requirements, and the potential for exquisite specificity of sulfur removal. (For a review, see Foght, cited above, pp. 379–407.)

BACKGROUND OF THE INVENTION

As early as 1953, ZoBell suggested that sulfur be removed from petroleum hydrocarbons by reduction and removal of hydrogen-reducible compounds by use of microbiological catalysts such as hydrogenases, including hydrogenases produced by sulfate-reducing microorganisms such as *Desulfovibrio desulfuricans* and Sporovibrio (U.S. Pat. No. 2,641,564). In one embodiment, he suggested that hydrogen for the reduction step be produced in situ by the action of a Clostridium, Aerobacter or other microorganism on carbohydrates (ibid., column 4, line 75 to column 6, line 25). Later researchers confirmed that sulfate-reducing bacteria can remove sulfur from petroleum using electrochemically supplied electrons (e.g., *Desulfovibrio desulfuricans* M6 described in Kim, et al., 1990, *Biotechnol. Lett.* 12: 757–760).

Though the validity of using an unsubstituted, low molecular weight model compound to select candidate microorganisms for desulfurization testing remains uncertain, because of its abundance in coal and oil and its refractory nature in chemical and physical desulfurizations, dibenzothiphene (herein abbreviated DBT) has become useful as a model for studying petroleum biodesulfurization (Fought, cited above, pp. 387–388). DBT is metabolized in bacteria by different metabolic pathways. In one pathway, a portion of the carbon DBT is metabolized without carbon-sulfur bond cleavage (id.). This pathway is undesirable from the standpoint of fossil fuel cleaning, since a portion of the organic structure of the molecule is destroyed and carbon-sulfur bond cleavage does not occur.

Another pathway of DBT metabolism is also carbon destructive, but carbon-sulfur bond cleavage occurs, releasing sulfite and sulfate. A Brevibacterium species denoted DO, for example, was reported to metabolize DBT as a sole source of carbon, energy, and sulfur, releasing sulfite (van Afferden, et al., 1990, *Arch. Microbiol.* 153: 324–328). Arthrobacter K3b metabolized DBT sulfone by a similar pathway, but was incapable of removing oxidized organic sulfur from Illinois No. 6 coal (Dahlberg, M. D., et al., 1993, *Fuel* 72: 1645–1650). *Sulfolobus acidocaldarius* reportedly oxidized DBT, forming sulfate (Kargi, F., and Robinson, J. M., 1986, *Fuel* 65: 397–399), but organic products of this metabolism were not determined, and it was unclear if the metabolism was carbon destructive. The organism reportedly removed 44% of organic sulfur from coal, although results with uninoculated controls were not reported.

Organisms that remove sulfur from DBT without destruction of the carbon ring structure appear to be most promising for possible application to fossil fuel desulfurization. Isbister and Kobylinski described a strain of Pseudomonas that produced sulfate and dihydroxybiphenyl from DBT (deposited in the A.T.C.C. as accession number 39381, U.S. Pat. No. 4,562,156 to Isbister, J. D., and Doyle). Isbister subsequently described an Acinetobacter strain CB2 (A.T.C.C. # 53515) that oxidized diphenyl sulfide and acted on organic sulfur in coal, but did not appear to remove thiophenic sulfur (U.S. Pat. No. 4,808,535).

Isolation after a selective mutation process led to the development of mutant *Rhodococcus rhodochrous* strain IGTS8 (U.S. Pat. No. 5,104,801 to Kilbane), an organism that metabolizes DBT via a pathway not destructive of the carbon rings of the molecule, and generated significant interest in the potential use of microorganisms for fossil fuel desulfurization. This organism has been deposited in the A.T.C.C. (accession no. 53968) and is the most widely studied bacterium considered for possible application to fossil fuel desulfurization. The organism metabolizes DBT as a sole source of sulfur, forming either 2-hydroxybiphenyl or 2,2'-dihydroxybiphenyl as a product (ibid.; Gallagher, J. R., et al., 1993, *FEMS Microbiol. Lett.* 107: 31–36; and Olson, G. J., 1993, *Fuel Processing Technol.* 40: 103–114), thus leaving the hydrocarbon portion of the molecule intact. Carbon-sulfur bond cleavage in DBT occurs, but sulfur does not accumulate in solution; it is apparently used immediately by the cells for biosynthesis (Gallagher, cited above).

The metabolic pathway of DBT degradation in *R. rhodochrous* IGTS8 under growing conditions proceeds via oxidation of the sulfur to the sulfoxide, sulfone, sulfonic acid, and the desulfurized product, 2,2'-dihydroxybiphenyl. Under resting conditions, the cells produce sulfoxide, 2'-hydroxybiphenyl-2-sulfinate and 2-hydroxybiphenyl (ibid.). The organism has been tested for its ability to desulfurize coal (Kilbane and Bielaga, cited above) and solubilized coal (Kilbane, J. J., and Jackowski, K., 1991, *Biotechnol. Bioengin.* 40: 1107–1114). However, since the organism uses sulfur in an assimilatory fashion, experimental systems require large amounts of cells to be applied to small amounts of coal. This limits the potential usefulness of a whole cell approach to coal biodesulfurization with this organism.

Moreover, it has generally been impossible to fully evaluate the validity of reports about organic sulfur removal from coal because insufficient data arepresented in support of the findings. The experimental deficiencies include reliance on indirect "organic sulfur" measurements, lack of appropriate experimental controls, and absence of data on coal recovery and associated elemental analyses (Olson, cited above, p. 104). Measurement of the "organic sulfur" content of coal is especially subject to error because the presence of elemental sulfur, metal sulfides, jarosites, and pyrites in some coals all lead to errors in indirect organic sulfur measurements. This is particularly true where significant biomass is associated with coal samples used because, since biomass has a much lower sulfur content than many coals, apparent desulfurization may occur due to dilution.

Nonetheless, R. rhodochrous or enzyme and/or membrane extracts of R. rhodochrous cultures (U.S. Pat. Nos. 5,132,219 and 5,344,778 to Kilbane) have been suggested in processes for the cleavage of organic C-S bonds in oil or coal (U.S. Pat. No. 5,358,869 to Kilbane), including continuous processes involving oxygenation and regeneration steps (U.S. Pat. No. 5,472,875 to Monticello), in combination with hydrodesulfurization for the "deep desulfurization" of liquid fossil fuels (U.S. Pat. Nos. 5,232,854 and 5,387,523 to Monticello), and in a process for the desulfurization and desalting of fossil fuels (U.S. Pat. No. 5,356,813 to Monticello).

Following publication of Kilbane's work on R. rhodochrous, other organisms have been described which appear to have similar metabolic pathways in the desulfurization of dibenzothiophene. These include a Bacillus sphaericus strain (A.T.C.C. Accession No. 53969, U.S. Pat. No. 5,002,888 to Kilbane), a strain identified as Corynebacterium sp. strain SY1 (Omori, T., et al., 1992, Appl. Environ. Microbiol. 58: 911–915), and a bacterium tentatively identified as R. erythropolis D-1 (Izumi, Y., et al., 1994, Appl. Environ. Microbiol. 60:223–226). These reportedly utilize DBT as a source of sulfur and produce 2-hydroxybiphenyl, releasing small amounts of sulfate. B. sphaericus A.T.C.C. 53969 requires a nutritional helper bacterium in order to metabolize DBT. Other strains of R. erythropolis have been described which convert DBT to monohydroxybiphenyl (Wang, P., and Krawiec, S., 1994, Arch. Microbiool. 161: 266–271); the presence of sulfate in the growth media repressed expression of desufurization activity, but sulfate added to suspensions of cells grown in DBT did not inhibit desulfurization activity. Gordona strain CYKS1 converts DBT to 2 hydroxybiphenyl (Rhee, S.-K., et al, 1998, Appl. Environ. Microbiol., 64: 2327–2331) Like Rhodococcus strain IGTS8, DBT metabolism was repressed by sulfate. The organism reportedly removed sulfur from diesel oils, although results from uninoculated controls were not given.

It would be desirable to have other, improved biocatalysts for the desulfurization of fossil fuels, especially agents that do not metabolize the fuel itself as a carbon and/or energy source. It would also be desirable to have fuel biodesulfurization agents isolated from natural sources that are economical and easy to cultivate.

DISCLOSURE OF THE INVENTION

It is an object of the invention to provide new microbiological methods for he desulfurization of fossil fuels.

It is another object of the invention to provide improved, natural desulfurization biocatalysts and screening methods for identifying them.

These and other objects are achieved by the present invention, which provides microorganisms that selectively remove sulfur from sulfur-containing fossil fuels without apparently utilizing the fuel as a carbon or energy source. In a typical biodesulfurization process, the microorganisms are incubated with fossil fuels for such time under such conditions to remove a portion, preferably at least about 20% by weight, of the sulfur from the fuel. In preferred embodiments, fuels are desulfurized as liquids by incubation with the microorganisms in liquid culture media containing basal salts and an assimilable carbon source devoid of sulfur, at about 25° to 30° C. for three to fourteen days in one or multiple stages. Fuels desulfurized as liquids include, but are not limited to, petroleum distillates and oils, synthetic fuels derived from petroleum and/or oils, and dissolved, solubilized, and/or emulsified viscous and solid hydrocarbon fuels. Carbon sources include, but are not limited to, glycerol, glucose, ethanol, sodium acetate, sodium succinate, sodium benzoate, sucrose, corn syrup, molasses, wastes obtained from sugar cane, manure, and/or mushroom compost, or mixtures thereof. Glycerol, glucose and/or ethanol are employed in some embodiments.

Microorganisms useful in the biodesulfurization methods of the invention are obtained and purified from soil or water samples. They arc first identified and biologically purified as microorganisms that grow on dibenzothiophene as a sole source of sulfur. After this preliminary step, they are then characterized in a two-step screen that first selects microbes that will utilize dibenzothiophene as a sole source of sulfur without metabolizing the phenyl ring structures of the compound, and then tests the microbes that utilize the sulfur only from DBT for their activity on fossil fuels. Organisms that remove sulfur from fossil fuels without apparently utilizing the fuels as a carbon or energy source are thus identified.

Briefly, microorganisms that will grow on dibenzothiophene as a sole source of sulfur are obtained incubating a soil or water sample in a bacterial culture medium containing inorganic nutrients, an assimilable carbon source devoid of sulfur, and dibenzothiophene as a sole source of sulfur for such time under such conditions sufficient to observe bacterial cell growth; diluting a culture that grows by a factor of 1:500 to 1:2000 with fresh culture medium at weekly intervals for at least three weeks to obtain an enriched culture; streaking the culture on a solid culture medium and incubating for such time under such conditions to obtain bacterial cell growth of isolated colonies; and restreaking isolated colonies to obtain biologically purified cultures of microorganisms that will grow on dibenzothiophene as a sole source of sulfur.

Purified cultures of microorganisms that will grow on dibenzothiophene as a sole source of sulfur are then screened first with dibenzothiophene and then with fossil fuel. The first screen comprises the steps of: (i) adding a purified culture to media containing inorganic nutrients, an assimilable carbon source devoid of sulfur, and dibenzothiophene as a sole source of sulfur, thereby providing a sample culture; (ii) adding the same purified culture to a second medium containing the same inorganic nutrients and carbon source, but no dibenzothiophene to obtain a control culture; (iii) incubating the sample and control for such time and under such conditions sufficient to observe bacterial cell growth; (iv) comparing the extent of growth in the sample culture containing the dibenzothiophene with the extent of growth in the control culture containing no dibenzothiophene; (v) identifying microorganisms that grow in the sample culture containing dibenzothiophene but do not grow in the control culture containing no benzothiophene; (vi) identifying the metabolic products of dibenzothiophene in a culture that grows on dibenzothiophene; and (vii) identifying as a positive first screen culture any microorganisms that grow on dibenzothiophene and yield metabolic products comprising biphenyls or hydroxybiphenyls and substantially no other products containing carbon.

Positive cultures are then rescreened in a second screen. In the second screen, a positive culture is inoculated into a bacterial culture medium containing inorganic nutrients and a fossil fuel as a sole carbon and sulfur source and also into a second corresponding culture containing the same bacterial culture medium, the same fossil fuel, and a second carbon source devoid of sulfur. Both cultures are incubated for such time under such conditions sufficient to observe purified culture cell growth, and the extent of growth in the culture containing the fossil fuel as the sole carbon source is compared to the extent of growth in the culture containing the fossil fuel and a second carbon source. Microorganisms that selectively remove sulfur from fossil fuels are identified by observing microbial growth in the culture in the presence of a fossil fuel and a second carbon source, and no growth of the corresponding culture incubated in the presence of the fossil fuel but no second carbon source.

The invention encompasses especially efficacious cultures identified in the screens, designated CDT-4 and CDT-4b, which were deposited in the A.T.C.C. on Aug. 10, 1998, and have not yet been granted accession numbers, and other microorganisms identified in the two-step screen, particularly those exhibiting biological desulfurization properties similar to strains CDT-4, which is a co-culture consisting of strains identified as a species of Pseudomonas and as *Nocardia asteroides*, and CDT-4b (the *Nocardia asteroides* component of CDT-4). These two organisms grow symbiotically in liquid and solid culture media.

BEST MODES FOR CARRYING OUT THE INVENTION

In the practice of this invention, soil or water microorganisms that selectively remove sulfur from fossil fuels are identified and isolated in a multi-step screening method, and then used to biodesulfurize fossil fuels. Microbial cultures that remove at least 20% of the sulfur from sulfur-containing fossil fuel samples are particularly preferred.

Biodesulfurization methods according to the invention are useful for the removal of sulfur from any sulfur-containing fossil fuel. As used herein, the term "fossil fuel" includes any hydrocarbon product derived from petroleum, coal, shale, oil, including crude oil, lignite, synthetic fuels derived therefrom, and mixtures thereof. Liquid fossil fuels such as petroleum distillates and light oils are particularly adaptable to desulfurization using methods of the invention because liquid fuels can be used as is without solubilization or emulsions. Viscous oils, bitumens, coal, and the like, on the other hand, are typically dissolved, solubilized and/or emulsified prior to desulfurization by biocatalysts of the invention using any dissolution, solubilization or emulsification method known to those skilled in the art, e.g., dissolving in hydrocarbon solvents such as alkanes or using emulsions such as those described in U.S. Pat. No. 5,539,889 to Valentine, for viscous hydrocarbons such as crude oil, or solubilizing as described by Kilbane and Jackowski, cited above, for coal. As used herein, when such viscous or solid fuels are rendered more fluid by emulsification, solubilization, suspension, and/or dissolution, they are also referred to as "liquid fuels" suitable for desulfurization in preferred embodiments of the invention employing liquid culture media.

A screening method for identifying soil or water microbes that selectively remove sulfur from fossil fuels typically involves a two-step procedure after cultures that appear promising in a prescreen with a model compound are isolated and biologically purified. In the prescreening step, soil or water samples are screened for microbial activity that indicates potential for fuel sulfur removal by testing metabolic activity in samples using a model sulfur compound. Any organic sulfur compound having a structure similar to sulfur compounds found in fossil fuels can be employed in this preliminary screening step. Sulfur compounds commonly occuring in fuels are preferred as models, particularly those that are refractory in the physical and chemical desulfurization methods described above. Model compounds that can be used are discussed by Foght, et al., cited above, and include, but are not limited to, thiophenes such as dibenzothiophene, benzothiophene, and alkylthiophenes, dibenzylsulfide, and the like. Because dibenzothiophene is both a common sulfur contaminant of crude oils and refractory, it was selected for use in the practice of a preferred embodiment of the invention. It is to be understood however, that the method of the invention could be adapted for screening of other organic sulfur contaminants in fuels by substitution of another model compound for dibenzothiophene.

Microorganisms having the capacity to metabolize sulfur-containing organic substrates are tested and grown in media that supply the organic and inorganic nutrients for good microorganism growth, but are typically devoid of inorganic and organic sulfur-containing compounds except those organic sulfur-containing compounds desired to be metabolized by the select microorganisms such as model compounds. Any type of liquid or solidified media that will support growth and reproduction of sulfur-metabolizing strains may be employed as cultures in the prescreening, screening and desulfurization methods of this invention. Several such media are known to the skilled worker. Example media include the basal salts medium providing mineral nutrients (inorganic salts of phosphate and nitrogen) described in the examples hereinafter, which contains $K_2HPO_4$, $NaH_2PO_4 \cdot H_2O$, $NH_4Cl$, $MgCl_2 \cdot 6H_2O$, $CaCl_2 \cdot 2H_2O$, $FeCl_3 \cdot 6H_2O$, and an assimilable carbon so devoid of sulfur; M9 minimal medium containing $Na_2HPO_4$, $KNaH_2PO_4$, $NH_4Cl$, $NaCl$, an assimilable carbon source devoid of sulfur, and, optionally, $CaCl_2$; and the like. Enriched media such as NZC broth prepared without cysteine or methionine and the like may also be employed, as well as mixtures of minimal and/or enriched media. Neutral, i.e., pH 6–7.5, media containing inorganic nutrients are preferred. Liquid media are also preferred, but media such as that solidified with agar using conventional methodology may also be employed in alternate embodiments.

Preferred microorganisms of the invention desulfurize fossil fuels without metabolizing the carbon structure of the fuel. Thus, screening steps of the invention are devised to identify microorganisms that will metabolize sulfur in the fuel but require a carbon source other than fuel. Some media for the screening steps therefore employ a microbiologically assimilable carbon source for nutrient and comparison purposes. Any assimilable carbon source that is preferably devoid of sulfur may be used in the media in amounts to support desired microbial growth. Suitable assimilable carbon sources include glycerol, glucose, and ethanol, or mixtures thereof. Sodium acetate, sodium succinate, sodium benzoate, sucrose, corn syrup, molasses, and the like, or wastes such as, but not limited to, sugar cane, manure, mushroom compost, or mixtures of these with each other or with the carbon sources listed above, may also be employed. Glycerol is used in one embodiment illustrated hereafter.

In the sulfur model compound preliminary screening step, a soil or water test sample is added to a bacterial culture medium containing inorganic nutrients, an assimilable carbon source devoid of sulfur, and dibenzothiophene (DBT) as a sole source of sulfur. The cultures are incubated with the test samples for such time and under such conditions sufficient to observe bacterial cell growth. In this prescreening step and in the screening steps described in greater detail hereafter, unless otherwise mentioned, incubations are typically carried out at atmospheric pressure in air at about 25° to 30° C. for three to fourteen days. Culture growth is evaluated by conventional methods. Where liquid cultures are employed, differences in growth are generally determined by observing and comparing turbidity; for this purpose, optical density (OD) readings between 550 to 650 nm, e.g., at 600 nm are made and compared. Microscopy may also be used to monitor growth of both liquid or solid media. With solid media, growth can additionally be assessed by visual inspection.

Incubations at this stage are typically carried out for at least three weeks. At weekly intervals, each culture is diluted 1:500 to 1:2000, preferably 1:1000 into fresh culture medium to enrich the strains that are growing. After the third transfer, the original environmental sample has been virtually completely diluted, and the positive test organisms present in the "enrichment culture" are capable of growth on DBT as a sole source of sulfur.

The enriched cultures are streaked on a standard solid culture medium such as nutrient or tryptone agar, and incubated for a few days. Several individual colonies that grow on the medium are restreaked onto fresh nutrient agar in order to obtain biologically purified cultures of microorganisms that will grow on dibenzothiophene as a sole source of sulfur. Generally, the purified culture consists of a single pure culture of microorganism. In some cases, two stains of organisms may grow symbiotically in liquid culture and intimately as single colonies containing both organisms on solid culture media. While not pure cultures, such co-cultures of organisms growing intimately associated and purified from environmental samples may metabolize DBT as efficiently or more so than single strains. An example cited above is *Bacillus sphaericus* ATCC No. 53969 which requires a nutritional helper bacterium to metabolize DBT.

The purified cultures are then screened in a first screen that characterizes their metabolic activity and identifies microorganisms that appear to have potential to desulfurize. In the first screen, the microorganisms are tested for their ability to grow on and metabolize DBT. A purified culture is inoculated into a medium containing inorganic nutrients, an assimilable carbon source devoid of sulfur and dibenzothiophene as a sole source of sulfur, thereby providing a sample culture. At the same time, a purified culture is inoculated into a corresponding second medium containing the same inorganic nutrients and carbon source, but no dibenzothiophene, thereby providing a control culture. The sample and control cultures are incubated for such time under such conditions sufficient to observe bacterial growth as evaluated by conventional methods such as turbidimetry or microscopy described above. Growth indicates and confirms the ability of a culture to use DBT as a sole source of sulfur, and indicates the culture is a candidate for removing sulfur from petroleum. Typical levels support significant growth, e.g., $10^9$ cells/ml. An inoculated flask not containing sulfur is used as a control for comparison purposes.

The identity of metabolic products of DBT metabolism is determined in the culture solutions using conventional analytic techniques such as chromatography, elemental analysis, mass spectrometry, or a combination of methods. Examples of analyses are illustrated hereafter. Thin layer chromatography is preferred in some embodiments. Media from cultures that grow on dibenzothiophene are analyzed, for example, for desulfurized products such as biphenyls or hydroxybiphenyls. Cultures are identified as positive qualitatively in the first screen if the metabolic DBT products contain biphenyls or hydroxybiphenyls and substantially no, i.e., less than about 5%, preferably less than about 1%, other products containing carbon. Preferred positive cultures show at least about a 20% desulfurization of dibenzothiophene and almost exclusive production of biphenyl or hydroxybiphenyl metabolic products.

Cultures that are identified as positive in the first screen are then rescreened in a second screen that evaluates desulfurization of fossil fuels. A positive culture from the first screen is inoculated into bacterial culture media containing inorganic nutrients and a fossil fuel as a sole carbon and sulfur source; the same positive culture is at the same time inoculated into a corresponding second culture containing the same bacterial culture media, the same fossil fuel, and a second carbon source devoid of sulfur. Liquid fossil fuels and liquid media are preferred. Both cultures are incubated for such time under such conditions sufficient to observe bacterial cell growth, and the extent of growth in the culture containing the fossil fuel as the sole carbon source is compared with the extent of growth in the culture containing the fossil fuel and a second carbon source. Microorganisms that selectively remove sulfur from fossil fuels are identified by observing microbial growth in a culture in the presence of a fossil fuel and a second carbon source, and no growth of the corresponding culture incubated in the presence of the fossil fuel but no second carbon source.

A distinct advantage of the screening methods of the invention is its simplicity. The protocol is straightforward. Many samples can be processed simultaneously. The screens yield a number of microorganisms exhibiting desulfurization capabilities suitable for the desulfurization of fossil fuels. One particularly advantageous microbial culture denoted CDT-4 in the examples and identified as a co-culture of *Nocardia asteroides* and a species of Pseudomonas, deposited in the A.T.C.C. on Aug. 10, 1998. The *Nocardia asteroides* component of CDT-4, designated CDT-4b, was also deposited in the A.T.C.C. on Aug. 10, 1998. Other preferred microorganisms are isolated by following the prescreening and screening steps outlined above and exhibit the biological desulfurization properties similar to CDT-4 and CDT-4b. Preferred strains exhibit at least 50% faster rate of DBT metabolism.

Isolated and purified desulfurization biocatalysts of the invention exhibit a number of desirable properties. The strains are readily cultured, exhibiting good growth rates on standard media supplemented with common carbon sources, and are capable of desulfurizing fossil fuels without metabolizing the carbon in the fuel.

In this respect, biocatalysts of the invention exhibit properties superior to some previously described. For example, the properties of one new desulfurization culture of the invention, CDT-4, described in greater detail in the examples hereinafter was compared (also as described in the examples) to *R. rhodocrous* (A.T.C.C. 53968), discussed above. The results can be summarized as follows:

|  | CDT-4 | ATCC 53968 |
|---|---|---|
| metabolizes DBT as a sulfur source | + | + |
| metabolizes DBT as carbon & energy source | – | – |
| relative rate of DBT metabolism | 1.9 | 1.0 |
| metabolizes distillate fuel oils as sulfur source | + | + |
| desulfurizes distillate fuel oils | + | + |
| metabolizes distillate fuel oil as carbon & energy source | – | + |

*R. Rhodochrous* metabolized the distillate as a source of carbon, but the biocatalyst of the invention did not. Thus, for desulfurization of the distillate, CDT-4 is superior.

Sulfur is removed from fossil fuels containing sulfur by contacting them with CDT-4, CDT-4b, or other microorganism of the invention, for such time and under such conditions to remove sulfur at least a portion of the sulfur from the fuel. Typically, this involves incubating a fossil fuel, particularly a liquid fossil fuel, with a culture of CDT-4, CDT-4b, or other microorganism of the invention, in a medium comprising mineral nutrients and an assimilable carbon source devoid of sulfur for such time under such conditions that at least a portion of the sulfur is removed. Examples of media and incubation conditions are those described for the screens above. In preferred embodiments, at least about 20% of the sulfur is removed.

Desulfurization biocatalysts of the invention may be used alone to treat fossil fuels, or in combination with other, e.g., previously-known, biocatalysts and/or with other methods. Examples of other methods that can be used with methods of the invention include, but are not limited to, separations of sulfur compounds such as that described by Johnson, et al., in U.S. Pat. No. 5,468,626 and hydrodesulfurization and bioremediation described by Monticello in U.S. Pat. No. 5,232,854, cited above. It is an advantage of the invention that the methods are useful for removing refractory sulfur not removable using other desulfurization methods.

EXAMPLES

The following examples are presented to further illustrate and explain the present invention and should not be taken as limiting in any regard.

Example 1

Enriched microorganism cultures that grew on DBT as a sole source of sulfur were isolated from refinery land farm soil in this example. As described below, qualitative test with Gibbs reagent indicated the presence of phenols in all culture solutions.

Organisms and Culture Conditions. *R. rhodochrous* strain IGTS8 was obtained from the American Type Culture Collection (ATCC 53968) and was maintained on nutrient agar. Other strains obtained from samples of soils taken from petroleum land farms near Billings, Mont. Soils were inoculated into basal salts medium (Olson et al 1993) containing DBT as the only added source of sulfur. The basal salts medium (BSM) lacked sulfur and carbon and energy sources and consisted of (in grams per liter of distilled water): $K_2HPO_4$, 4.0; $NaH_2PO_4.H_2O$, 4.6; $NH_4Cl$, 2.0; $MgCl_2.6H_2O$, 0.2; $CaCl_2.2H_2O$, 0.001; and $FeCl_3.6H_2O$, 0.001. The medium was sterilized by autoclaving at 121° C. for 15 min. The phosphate salts were autoclaved separately and combined with the remaining medium when cool. The pH of the medium was 6.5. DBT was added at a final concentration of 0.2 mM from a 100 mM stock solution in ethanol. Glycerol was used as the carbon and energy source. It was added at a final concentration of 0.2% from a sterile 20% solution.

Soil samples (0.5 g) were inoculated into 125 ml Erlenmeyer flasks containing 50 ml of basal salts medium supplemented with glycerol (0.2%) and DBT (0.2 mM). After 12 days incubation of 25° C., 0.1 ml was transferred into 50 ml of fresh medium. This step was repeated twice more at 10 day intervals. After 4 successive subcultures, sulfur in the initial soil had been virtually eliminated and the cells growing in the culture could only be obtaining sulfur for their growth requirements from DBT. The enrichment cultures were streaked on nutrient agar, and after 2 to 3 days, several colonies of different appearance were restreaked twice on fresh nutrient agar plates. The isolates were transferred to nutrient agar slants, and additional tests were conducted on these nine isolates.

Chemical Analyses. Gibbs reagent (2,6-dichloroquinone-4-chloroimide, Sigma) was used to measure the production of phenolic compounds in culture solutions (Kibane and Bielaga, 1991). The reagent was prepared in ethanol at a concentration of 10 mg/ml. The assay was conducted by adding 0.16 ml of 10% (w/v) sodium carbonate to 5.0 ml of centrifuged (4000×g for 10 min) culture medium followed by 0.05 ml of Gibbs reagent. A blue color developed in the presence of phenols. The absorbance of the solution at 610 nm was measured after 30 min. A calibration curve was prepared from authentic 2-phenylphenol (2-hydroxybiphenyl, Aldrich).

The layer chromatography (TLC) was employed further identify products of DBT metabolism in culture solutions. Centrifuged culture solutions (20 ml) were acidified with 6M HCl (0.5 ml) and extracted twice with 2 ml portions of chloroform. The extracts were combined with evaporated to about 0.2 ml. Aliquots of 10 to 50 µl were spotted on silica gel (Kieselgel 60) TLC plates that were previously heated at 120° C. for 20 minutes. Authentic DBT, 2-hydroxybiphenyl (2 mg/ml) and 2,2-biphenol (dihydroxybiphenyl, Aldrich, 4 mg/ml) were prepared in chloroform and applied (10 µl) as references. TLC plates were placed in tanks with chloroform as the mobile phase. After air drying, the TLC plates were examined under the short wave UV light.

Sulfate was determined by turbidimetry following treatment with barium chloride (ASTM, 1989). The detection limit of this technique is 1 to 2 mg/l sulfate (0.01 to 0.02 mM).

Example 2

Bacterial cultures identified in Example 1 as utilizing DBT as a sole source of sulfur were further screened for desulfurization of distillate fuel oil in this example.

Tests with Distillate Fuel Oil. A No. 2 distillate fuel oil certified to contain 0.33% sulfur was obtained from the National Institute of Standards and Technology (NIST standard reference material 1624b). Aliquots of 1.0 to 2.0 ml of the oil were added to 50 ml (test 1 below) or one liter of BSM (remaining tests below) containing 0.2% glycerol in one liter screw capped glass bottles. Bottles were inoculated with actively growing cells from BSM plus glycerol and DBT. Incubation was at 25° C. with gentle agitation at 100 rpm on an orbital shaker. Control tests remained uninoculated.

Several tests of petroleum biodesulfurization were undertaken. The first test involved a single stage 5 day treatment of distillate with R. rhodochrous IGTS8. Triplicate inoculated and uninoculated flasks were tested. Following biotreatment, the fuel oil was recovered by pipette. Some of the oil formed an emulsion with the culture medium and to fully recover the oil it was necessary to break the emulsion by centrifugation at 1000×g for 10 min. The remaining tests were conducted with culture CDT-4 and were conducted in two stages. The tests were inoculated with 0.05 ml of cells grown on BSM, glycerol and DBT to give an initial concentration of $10^5$ cells/ml. After reaction in the first stage for 10 to 14 days, 800 to 900 ml of culture solution was removed (the oil remained) and fresh culture medium added to the remaining culture containing the distillate to effect a 2 stage treatment of the distillate.

The recovered distillate was submitted to Huffman Laboratories, Golden, CO for elemental analysis. In addition, a portion of the sample was analyzed by low voltage high resolution mass spectroscopy (HRMS) at the Pittsburgh Energy Technology Center. The HRMS provides data on total sulfur and on functional groups present in fossil fuels.

Bacterial Cultures. Eight bacterial cultures obtained from the enrichment cultures described in Example 1 above were tested to determine if they could also metabolize sulfur in distillate fuel oil as a sole sulfur source (Table 1, below). R. rhoclochrous ATCC 53968 (IGTS8) was included for comparative purposes. None of the organisms grew in the basal medium alone or in basal medium plus glycerol. If DBT and glycerol were added to the basal medium, growth of all cultures occurred. If glycerol and distillate fuel oil were added to the basal medium, all cultures grew. These results indicated that all cultures can obtain sulfur for growth from distillate fuel oil and from DBT.

TABLE 1

Growth of Organisms in BSM with Various Carbon and Sulfur Sources.

| Culture | BSM Alone | BSM + Glycerol | BSM + glycerol + DBT | BSM + glycerol + distillate | BSM + distillate |
|---|---|---|---|---|---|
| CDT-1 | − | − | + | + | − |
| CDT-2 | − | − | + | + | + |
| CDT-3 | − | − | + | + | + |
| CDT-4 | − | − | + | + | − |
| CDT-5 | − | − | + | + | − |
| CDT-6 | − | − | + | + | + |
| CDT-7 | − | − | + | + | − |
| CDT-8 | − | − | + | + | − |
| IGTS8 | − | − | + | + | + |

(+) indicates growth after 2 weeks incubation, (−) indicates no growth

Additional tests showed that when distillate fuel oil alone was added to the basal medium, 4 of the 9 cultures grew, including R. rhodochrous. This indicates that these metabolize distillate fuel oil as a sole source of sulfur, carbon and energy. Thus, a portion of the hydrocarbon value of the distillate fuel was metabolized. Five of the cultures failed to grow in basal salts medium plus distillate fuel oil. This indicates these organisms could not metabolize distillate fuel oil. These 5 cultures were candidates for further testing.

Products of DBT metabolism. The ability of R. rhodochrous to form 2-hydroxybiphenyl from DBT was confirmed. After 3 days of growth of the organism in a shake flask on BSM plus glycerol (0.2%) and DBT (0.2 mM), the concentration of 2-hydroxybiphenyl as determined by Gibbs assay was 0.04 mM, corresponding to 20% conversion of DBT. Thin layer chromatography of culture extracts showed spots with Rf identical to DBT and monohydroxybiphenyl (Table 2). The uninoculated control showed a single spot corresponding to DBT. When authentic 2-hydroxybiphenyl and dihydroxybiphenyl were spiked into the culture extract and chromatographed, the spot corresponding to 2-hydroxybiphenyl became brighter, and new spot corresponding to dihydroxybiphenyl appeared.

TABLE 2

Products of DBT Metabolism Determined by TLC.

| organism/model compound | Rf | identity |
|---|---|---|
| DBT | 0.90 | |
| 2-hydroxybiphenyl (2HBP) | 0.61 | |
| Dihydroxybiphenyl (DHB) | 0.18 | |
| CDT-1 | 0.89, 0.56 | DBT, 2HBP |
| CDT-2 | 0.90, 0.58 | DBT, 2HBP |
| CDT-3 | 0.92, 0.58 | DBT, 2HBP |
| CDT-3 spiked[1] | 0.91, 0.56, 0.16 | DBT, 2HBP, DHB |
| CDT-4 | 0.89, 0.61 | DBT, 2HBP |
| CDT-5 | 0.89, 0.56 | DBT, 2HBP |
| CDT-6 | 0.90, 0.59 | DBT, 2HBP |
| CDT-7 | 0.90, 0.57 | DBT, 2HBP |
| CDT-8 | 0.90, 0.58 | DBT, 2HBP |
| control (uninoculated) | 0.90 | DBT |
| R. rhodochrous | 0.91, 0.61 | DBT, 2HBP |
| R. rhodochrous spiked[1] | 0.89, 0.59, 0.16 | DBT, 2HBP, DHB |

[1]extract spiked with 10 μl each of authentic DBT, MHB, DHB in chloroform

The eight soil cultures also produced phenolic compounds when grown in basal salts medium plus glycerol and DBT as indicated by Gibb's reagent. Additional tests with TLC showed that the cultures produced 2-hydroxybiphenyl as the sole detectable product (Table 2). This product was not detected in uninoculated solutions containing DBT. Sulfate was not detected in culture solutions, nor was the odor of hydrogen sulfide detected. These results indicate that the eight cultures probably metabolize DBT by a pathway similar to R. rhodochrous.

The kinetics of growth and DBT conversion were tested with the eight cultures and R. rhodochrous. After 64 hours of growth, strain CDT-4 had grown to the highest turbidity and had produced the largest amount of phenolic material as determined by Gibb's assay (Table 3).

TABLE 3

Cell growth (absorbance at 600 nm) and DBT conversion[1]

| | A600 | % DBT conversion |
|---|---|---|
| CDT-1 | 2.00 | 26 |
| CDT-2 | 1.68 | 20 |
| CDT-3 | 1.79 | 25 |
| CDT-4 | 2.28 | 26 |
| CDT-5 | 1.48 | 19 |
| CDT-6 | 1.82 | 20 |
| CDT-7 | 1.44 | 17 |
| CDT-8 | 1.21 | 14 |
| IGTS8 | 1.23 | 15 |

[1]cells grown in 50 ml of BSM in 250 ml Erlenmeyer flasks with 0.2 mM DBT and 0.2% glycerol for 64 hours at 30° C., 180 rpm. DBT conversion to phenolic product was quantified colorimetrically using Gibb's reagent.

CDT-4 was selected for additional tests with distillate fuel oil. This culture is a mix of two bacterial strains. One is a gram-negative motile rod, occurring singly or in pairs when grown in BSM with glycerol and sulfate and identified as a species of Pseudomonas by membrane fatty acid analysis.

The other culture was similarly identified as *Nocardia asteroides*. It is non-motile, irregular, gram-positive rod, sometimes occurring in V shapes or in a branching morphology.

Only the *Nocardia asteroides* component (CDT-4b) of the CDT-4 culture metabolized DBT. The Pseudomonas species did not grow on DBT as a sole source of sulfur and did not form phenolic products from DBT as determined by Gibbs assay. The Nocardia species did not require the presence of the Pseudomonas species to metabolize DBT. Tests with Gibbs assay showed *Nocardia asteroides* metablized DBT about twice as fast at 27° C. as at 21° C. DBT was not metabolized by the organism at 35° C. As shown below, the Nocardia species also removed sulfur from diesel fuel in the absence of the Pseudomonas species. Though the Pseudomonas species is not necessary for the metabolism of DBT or the desulfurization of diesel fuel by the Nocardia organism, the organism in co-culture may scavenge sulfate from the culture solution. Sulfate in culture media represses the metabolism of DBT by the Nocardia species. Consequently, the scavenging of sulfate by the faster growing Pseudomonas strain could reduce lag times or prevent accumulation of sulfate in culture solutions, leading to more efficient degradation of DBT by *Nocardia asteroides*.

Tests with Distillate Fuel Oil

Initial biodesulfurization tests were conducted in 50 ml of the culture solution with *R. rhodochrous* IGTS8. Elemental analyses suggested desulfurizaton of distillate fuel oil by the organism (Table 4, test 1; Table 5). However, subsequent attempts to achieve higher levels of biodesulfurization with this organism were unsuccessful. These tests employed 2-stage treatment of distillate in larger (1-liter) volumes of culture medium for longer time periods. It was impossible to recover oil from the emulsions that formed in these tests. Since this organism can grow on distillate as a sole source of carbon and energy, it is possible that biodegradation of the fuel oil was proceeding. This process may not have been evident in the initial short term test at a small (50 ml) volume.

A test of desulfurization distillate fuel oil was conducted with the two cultures that grew best on DBT: CDT-1 and CDT-4 (Table 4, Test 2). Elemental analyses provided evidence that CDT-4 removed sulfur from distillate fuel oil but CDT-1 did not. In these tests, CDT-4 grew much better than CDT-1, reaching a cell density of 1.6 and $1.1 \times 10^8$/ml after first and second stage treatment, respectively. CDT-1 reached cell densities of $4.0 \times 10^7$ cells/ml at the end of both stages of treatment.

Another test (Table 4, test 3) with strain CDT-4 provided further evidence of biodesulfurization of oil. However, the sulfur content of oil recovered from one of the control flasks was inexplicably low. In this test, CDT-4 grew in BSM, glycerol and oil with a doubling time of 6 days, reaching a cell density of $9 \times 10^7$ cells after first stage treatment and $7 \times 10^7$ cells/ml after second stage treatment. The corresponding cell biomass yields were 28 and 26 mg dry cells. The sulfur content of CDT-4 biomass is not known. However, if it is 1%, as in *Escherichia coli* biomass (reported by Bailey, J. E., and Ollis, D. F., 1977, *Biochemical Engineering Fundamentals*, McGraw-Hill, New York), page 28, this yield of CDT-4 cells would have removed 15% of the mass of sulfur in the oil.

TABLE 4

Results of distillate fuel oil biodesulfurization tests

| | # flasks | mean % S (std.dev) in recovered oil | mean % biodesulfurization (versus control) |
|---|---|---|---|
| Test 1 control | 3 | 0.37 (0.010) | |
| IGTS8 | 3 | 0.032 (0.015) | 14 |
| Test 2 control | 1 | 0.42 | |
| CDT-1 | 1 | 0.45 | 0 |
| CDT-4 | 1 | 0.24 | 43 |
| Test 3 control | 2 | 0.31 (0.099) | |
| CDT-4 | 2 | 0.25 (0.014) | 19 |
| Test 4 control | 2 | 0.30 (0.035) | |
| CDT-4 | 2 | 0.24 (0.007) | 20 |

A fourth test also provided evidence of distillate fuel oil desulfurization by CDT-4 (Table 4) as determined by elemental analysis of the recovered oil. Further measurements of the recovered oil by low voltage high resolution mass spectroscopy confirmed the loss of sulfur in biotreated oil and further indicated that aromatic sulfur was being removed from the distillate by the biocatalyst (Table 5).

TABLE 5

High Resolution Mass Spectral Analysis of Biotreated and Control Distillate

| | % BT | % DBT | % S |
|---|---|---|---|
| Control | 1.81 | 2.27 | 0.83 |
| | 1.81 | 2.53 | 0.86 |
| CDT-4 | 1.50 | 2.00 | 0.67 |
| | 1.50 | 2.26 | 0.68 |
| % bioremoval | 17 | 13 | 20 |

% BT: % of total ion intensity associated with alkyl benzothiophenes; % DBT: % total ion intensity associated with alkyl dibenzothiophenes; % S: weight % S. The BT and DBT fractions make up the vast majority of sulfur in the distillate. 2-hydroxybiphenyl as a standard.

Elemental analyses were close to 100% in all recovered oil (Table 6). Recovery of the fuel oil following biotreatment was 85% in the short term tests with *R. rhodochrous* but only about 70% in longer term, 2 state tests with CDT-4 (Table 5). Recovery of oil was similar in control and inoculated flasks, indicating that incomplete oil recovery is probably not due to the presence of metabolism of the cells. Very finely dispersed oil in water may have eluded recovery.

TABLE 6

Elemental Analyses of Distillate Recovered from Biodesulfurization Tests

| | % recovery | % C | % H | % O | % N | % S | sum |
|---|---|---|---|---|---|---|---|
| TEST 1[1] | | | | | | | |
| IGTS8 | 84 | 87.17 | 12.18 | 0.10 | 0.14 | 0.32 | 99.90 |
| | | (0.09) | (0.13) | (0.03) | (0.02) | (0.02) | (0.23) |
| control | 85 | 87.21 | 12.24 | 0.14 | 0.09 | 0.37 | 100.05 |
| | | (0.39) | (0.08) | (0.04) | (0.02) | (0.01) | (0.51) |
| TEST 2 | | | | | | | |
| CDT-1 | 71 | 87.19 | 11.94 | 0.64 | 0.05 | 0.45 | 100.27 |
| CDT-4 | 67 | 87.15 | 12.42 | 0.78 | 0.07 | 0.24 | 100.66 |
| Control | 73 | 87.14 | 12.01 | 0.73 | 0.06 | 0.42 | 100.36 |

TABLE 6-continued

Elemental Analyses of Distillate Recovered from Biodesulfurization Tests

| | % recovery | % C | % H | % O | % N | % S | sum |
|---|---|---|---|---|---|---|---|
| TEST 3[2] | | | | | | | |
| CDT-4 | 68 | 86.24 | 12.67 | 1.18 | 0.01 | 0.24 | 100.34 |
| | 70 | 86.21 | 12.65 | 1.31 | 0.01 | 0.26 | 100.44 |
| Control | 73 | 86.02 | 12.29 | 1.45 | 0.01 | 0.38 | 100.15 |
| | 74 | 85.91 | 12.57 | 1.61 | 0.01 | 0.24 | 100.34 |
| TEST 4[2] | | | | | | | |
| CDT-4 | 67 | 86.41 | 12.56 | 0.97 | 0.02 | 0.23 | 100.19 |
| | 72 | 86.57 | 12.59 | 0.99 | 0.01 | 0.24 | 100.40 |
| Control | 68 | 86.84 | 12.67 | 1.03 | 0.01 | 0.27 | 100.82 |
| | 76 | 86.67 | 12.64 | 1.05 | 0.01 | 0.32 | 100.69 |

[1]standard deviation of triplicate flasks in parentheses ( ).
[2]results of duplicate flasks shown Tests were done also to determine if the Nocardia component of CDT-4 alone could remove sulfur from diesel fuel. In these tests, NIST SRM 2724a, diesel fuel certified to contain 0.043% S, was used as the test substrate. The results shown in tables 7 and 8 provide evidence that treatment of diesel fuel with *Nocardia asteroides* (CDT-4b) alone removes significant amounts of sulfur from diesel fuel.

A single stage test with 1.5 g of diesel fuel added to duplicate flasks containing 500 ml of culture medium containing *Nocardia asteroides* was conducted for 20 days at 27° C. Duplicate control flasks containing diesel fuel but remaining uninoculated were tested also. Analysis of the recovered diesel fuel indicated that (Table 7) significant sulfur was removed in the presence of *Nocardia asteroides* whereas no sulfur was lost from diesel fuel in controls. Solutions from inoculated flasks contained five-fold higher phenol content by Gibbs assay than solutions from control flasks.

TABLE 7

Analysis of diesel fuel recovered from flasks inoculated with *Nocardia asteroides* and from uninoculated (control) flasks.

| | % S | % loss S[1] |
|---|---|---|
| Nocardia | 0.028 | 34.9 |
| | 0.025 | 41.9 |
| Control | 0.047 | 0 |
| | 0.047 | 0 |

[1]based on certified value of 0.043% S in starting material.

A two-stage test of diesel fuel biodesulfurization was conducted in triplicate with *Nocardia asteroides*. In this test, 1.5 g of diesel fuel was added to 500 ml of culture medium and flasks were inoculated. Controls remained uninoculated. The sulfur content of the diesel fuel recovered from inoculated flasks was significantly lower than controls after 24 days (Table 8).

TABLE 8

Analysis of diesel fuel (NIST 2724a) recovered from triplicate two stage tests

| | % S | % loss S[1] |
|---|---|---|
| Nocardia | 0.020 | 52.9 |
| | 0.018 | 57.7 |
| | 0.016 | 62.4 |
| mean | 0.018 | 57.7 |
| s.d. | 0.002 | |
| control | 0.036 | 15.3 |
| | 0.028 | 34.1 |
| | 0.032 | 24.7 |
| mean | 0.032 | 24.7 |
| s.d. | 0.004 | |

[1]based on certified value of 0.043% S in starting material.

CDT-4, a co-culture consisting of *Nocardia asteroides* and a species of Pseudomonas, and CDT-4b, the *Nocardia asteroides* component of CDT-4, were deposited in the American Type Culture Collection (A.T.C.C.), 10801 University Boulevard, Manassas, Va. 20110–2209 on Aug. 10, 1998, and bear accession numbers 202161 and 202160, respectively. These deposits were made in under and in accord with the Budapest Treaty and all restrictions imposed by the depositor on the availability to the public of the deposited biological material will be irrevocably removed upon granting of the patent.

All papers and patents cited above are hereby incorporated herein in their entireties by reference.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. A biologically purified microbial co-culture, CDT-4, of species of Pseuclonionas, and a species of *Nocardia asteroides*, CDT-4b.

2. A method for removing sulfur from a fossil fuel containing sulfur comprising incubating the fuel with a culture according to claim 1 in a media comprising mineral nutrients and an assimilable carbon source devoid of sulfur for such time under such conditions to remove at least a portion of the sulfur in said fuel.

3. A method according to claim 2 wherein at least about 20% of the sulfur is removed in an incubation at about 25° to 30° C. for about fourteen to 24 days.

4. A method according to claim 2 wherein the media is a basal salts media and the assimilable carbon source is selected from the group consisting of glycerol, glucose, ethanol, and mixtures thereof.

5. A method according to claim 2 wherein the fossil fuel is liquid and the culture media is a liquid.

6. A method according to claim 5 wherein the fossil fuel is a petroleum distillate.

7. A method for removing sulfur from a liquid fossil fuel containing sulfur comprising incubating the fuel with a microbial cultures CDT-4 or CDT-4b in a liquid media comprising basal salt nutrients and an assimilable carbon source devoid of sulfur for such time under such conditions effective to remove at least a portion of the sulfur in the fuel.

8. A method according to claim 7 wherein at least about 20% of the sulfur is removed.

9. A screening method for identifying and purifying soil or water microorganisms that selectively remove sulfur from fossil fuels, which comprises:

(a) first isolating and biologically purifying microorganisms that will grow on dibenzothiophene as a sole source of sulfur by
  (i) incubating a soil or water sample in a bacterial culture media containing inorganic nutrients, an assimilable carbon source devoid of sulfur, and dibenzothiophene as a sole source of sulfur for such time under such conditions sufficient to observe bacterial cell growth;
  (ii) diluting a culture that grows by a factor of 1:500 to 1:2000 with fresh culture media at weekly intervals for at least three weeks to obtain an enriched culture;
  (iii) streaking the culture on a solid culture medium and incubating for such time under such conditions to obtain bacterial cell growth of isolated colonies; and
  (iv) restreaking isolated colonies to obtain biologically purified cultures of microorganisms that will grow on dibenzothiophene as a sole source of sulfur;

(b) then screening the biologically purified cultures in a first screen comprising the steps of:
  (i) adding a purified culture from step (a) to media containing inorganic nutrients, an assimilable carbon source devoid of sulfur, and dibenzothiophene as a sole source of sulfur, thereby providing a sample culture;
  (ii) adding the purified culture to a corresponding second media containing the same inorganic nutrients and carbon source, but no dibenzothiophene, thereby providing a control culture;
  (iii) incubating the sample and control cultures for such time and under such conditions sufficient to observe bacterial cell growth;
  (iv) comparing the extent of growth in the sample culture containing the dibenzothiophene with the extent of growth in the culture containing no dibenzothiophene;
  (v) identifying any culture that grows in the sample culture containing dibenzothiophene but does not grow in the control culture containing no dibenzothiophene;
  (vi) identifying the metabolic products of dibenzothiophene in any cultures that grows on dibenzothiophene; and
  (vii) identifying as a positive first screen culture any culture that grows on dibenzothiophene and yields metabolic products comprising biphenyls or hydroxybiphenyls and substantially no other products containing carbon; and then (c) rescreening the positive cultures identified in (b) in a second screen comprising the steps of:
  (i) inoculating, with a positive culture identified in screen (b), a bacterial culture media containing inorganic nutrients and a fossil fuel as a sole carbon and sulfur source;
  (ii) inoculating, with the same positive culture, a corresponding second culture containing the same bacterial culture media, the same fossil fuel, and a second carbon source devoid of sulfur;
  (iii) incubating the cultures for such time under such conditions sufficient to observe bacterial cell growth;
  (iv) comparing the extent of growth in the culture containing the fossil fuel as the sole carbon source with the extent of growth in the culture containing the fossil fuel and a second carbon source;
  (v) identifying a microorganism that selectively removes sulfur from fossil fuels by observing microbial growth in a culture in the presence of a fossil fuel and a second carbon source, and no growth of the corresponding culture incubated in the presence of the fossil fuel but no second carbon source.

10. A method according to claim 9 wherein only first screen positive test samples that desulfurize at least about 20% of the dibenzothiophene in the first screen culture are tested in the second screen.

11. A method according to claim 9 wherein the incubations in both screens are conducted at about 25° to 30° C. for three to fourteen days.

12. A method according to claim 9 wherein the carbon source is selected from the group consisting of glycerol, glucose, ethanol, and mixtures thereof, and the media for both screens is a basal salts media.

13. A method according to claim 12 wherein the carbon source is glycerol.

14. A biological purified microbial culture of *Nocardia asteroides, CDT*-4b.

* * * * *